United States Patent [19]

Ohkubo et al.

[11] Patent Number: 4,762,412
[45] Date of Patent: Aug. 9, 1988

[54] OPTICAL SCANNING DEVICE

[75] Inventors: Kunihiko Ohkubo; Shunichiro Sasaki, both of Kyoto, Japan

[73] Assignee: Shimadzu Corporation, Kyoto, Japan

[21] Appl. No.: 813,140

[22] Filed: Dec. 24, 1985

[30] Foreign Application Priority Data

Dec. 26, 1984 [JP] Japan .................................. 59-275164
Dec. 27, 1984 [JP] Japan .................................. 59-277562
Dec. 29, 1984 [JP] Japan .................................. 59-275871

[51] Int. Cl.$^4$ ................................................ G01J 3/42
[52] U.S. Cl. .................................... 356/319; 350/272; 356/73; 356/308
[58] Field of Search ................ 358/202, 203; 356/386, 356/73, 300, 304, 308, 309, 310, 319, 326, 328, 331-334, 443, 444; 350/6.1, 272-275

[56] References Cited

U.S. PATENT DOCUMENTS

| 2,078,768 | 4/1937 | Meier | 356/326 |
| 3,016,464 | 1/1962 | Bailey | 350/6.1 X |
| 3,259,733 | 7/1966 | Klaver et al. | 358/202 |
| 3,671,754 | 6/1972 | Mundkur | 350/272 X |
| 3,768,913 | 10/1973 | Klimecki | 356/444 |
| 3,994,587 | 11/1976 | Yamamoto et al. | 356/444 |
| 4,013,364 | 3/1977 | Nakano et al. | 250/557 |
| 4,145,139 | 3/1979 | Nakamura et al. | 356/444 |
| 4,150,899 | 4/1979 | Nakamura | 356/444 |
| 4,227,811 | 10/1980 | Tohyama et al. | 356/325 |
| 4,243,325 | 1/1981 | Ernst | 350/272 |
| 4,305,663 | 12/1981 | Perkins et al. | 356/325 |
| 4,544,271 | 10/1985 | Yamamoto | 356/328 |

FOREIGN PATENT DOCUMENTS 0765667  9/1980  U.S.S.R. .............................. 356/444

OTHER PUBLICATIONS

Heinecke et al., *Nuclear Instruments and Methods*, 133, No. 2, 3/1/76, p. 283.
Olson, *Rev. Sci. Inst.*, vol. 31, No. 8, pp. 844–849, Aug. 1960.
White, *Conference: Proceedings of the Seminar on Remote Sensing of Earth Resources and the Environment*, Palo Alto, Calif., Nov. 1971, pp. 111–114.

Primary Examiner—F. L. Evans
Attorney, Agent, or Firm—Finnegan, Henderson, Farabow, Garrett & Dunner

[57] ABSTRACT

An optical scanning device, such as a chromatoscanner, includes a spectroscope having a rectangular outlet slit for producing a light beam in the shape thereof. A rotatable disk having a spiral slit is disposed in the path of the light beam to produce light pulses along radial lines of the disk which are directed to the surface of a specimen. The absorbancy of the light pulses at discrete positions of the specimen is measured and stored in a memory in accordance with the corresponding location on the specimen as derived from measuring the rotation angle of the disk.

9 Claims, 4 Drawing Sheets

OPTICAL SCANNING DEVICE

FIELD OF THE INVENTION

This invention relates to an optical scanning device and, more particularly; to a chromatoscanner employed in a transmission or reflection type densitometer which optically scans a specimen on a thin plate or a thin layer of a specimen within an electrophoresis gel.

BACKGROUND OF THE INVENTION

In measuring the absorbancy of a specimen with a conventional chromatoscanner, a fixed light beam is applied to a specimen under measurement and the stage supporting the specimen is moved in the X direction and in the Y direction so that the light beam scans the specimen in a zigzag manner. However, the method of moving the stage while maintaining the specimen in a fixed position is disadvantageous because the large inertial force of the stage limits, to a certain degree, the ability to increase scanning speed. Examples of devices of the prior art include U.S. Pat. Nos. 3,994,587, 4,013,364, 4,145,139 and 4,150,899.

In order to eliminate the above-described drawback, a so-called "flying spot type" chromatoscanner has been proposed in which the light beam applied to the specimen is moved. In the chromatoscanner, in order to scan the specimen with the light beam it is necessary to swing a light beam focusing mirror about a rotary shaft or to swing a slit whose configuration is similar to the section of the light beam to be focused on the specimen. Where it is required to provide a high-speed chromatoscanner, however, the method of swinging the mirror (or rotating the mirror in one direction) is unacceptable in that the inertia of the mirror determines the upper limit of the scanning speed. The method of swinging the slit is disadvantageous in that, since it is required to rotate the motor (which is generally a step motor) frequently and alternately in the forward direction and the reverse direction, it is impossible to rotate the motor at high speed.

OBJECTS AND SUMMARY OF THE INVENTION

In view of the foregoing, an object of the present invention is an optical scanning device of simple construction in which a light beam applied to a specimen is moved for high-speed scanning operations.

Another object of the present invention is an optical scanning device in which the variation in sensitivity of a detector depending on the positions on a light receiving surface can be corrected.

A further object of the present invention is a chromatoscanner in which a part of the scanning light beam is monitored at all times to give suitable feedback control to measuring photomultipliers.

Yet another object of the present invention is a chromatoscanner in which the measurement range can be adjusted according to the size of a specimen under measurement.

These and other objects are accomplished by a device for optically scanning a specimen comprising means for producing a light beam, a rotatable disk in the path of the light beam, the disk having a reading slit therein formed a distance from the center of the disk which increases with increasing angle of rotation of the disk, and means for rotating the disk to produce light pulses directed at the specimen, the rotation angle of the rotating means corresponding to the position on the specimen sample irradiated by the light pulses.

BRIEF DESCRIPTION OF THE DRAWINGS

The foregoing objects and other objects of the present invention will become more apparent from the following detailed description and the appended claims when read in conjunction with the accompanying drawings, wherein:

DETAILED DESCRIPTION

Figure 1:
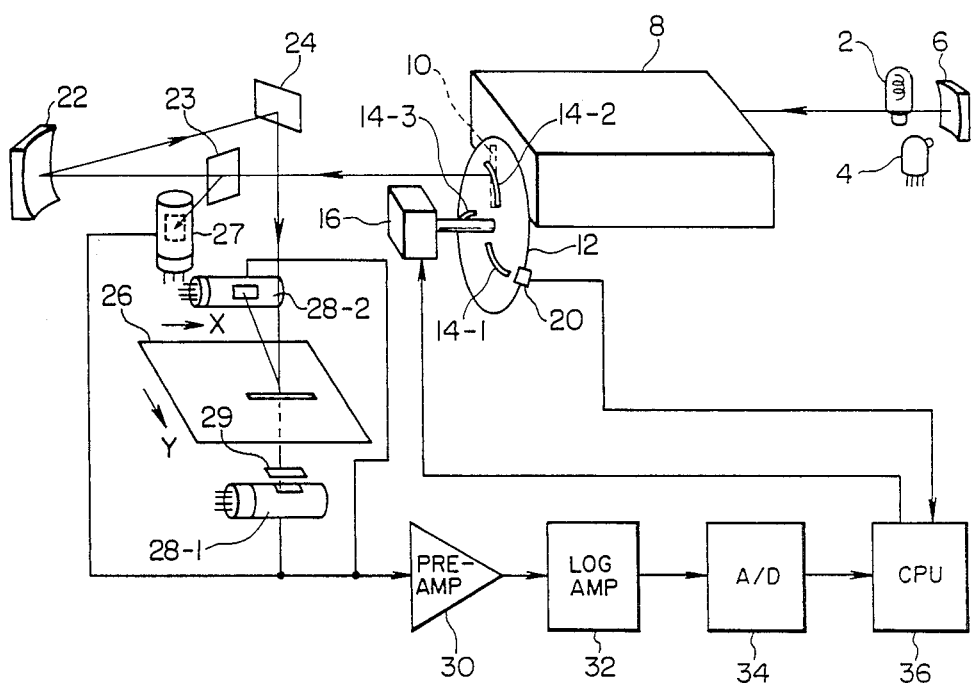
FIG. 1 is an explanatory diagram, partly as a block diagram, showing the arrangement of one example of an optical scanning device using a chromatoscanner according to the present invention.

FIG. 1 shows one example of a densitometer using a chromatoscanner with an optical scanning device according to the present invention. In FIG. 1, reference numerals 2 and 4 designate light sources. In order to provide a wide range of measurement wavelengths, two kinds of light sources are provided which are selected, for example, from the group of xenon, tungsten, and heavy hydrogen lamps. A spherical mirror 6 selects one of the light sources 2 and 4 to apply the light beam from the light source 2 or 4 to a spectroscope 8. A light beam in the form of a spectrum emerges from the outlet slit 10 of the spectroscope 8.

Figure 2:
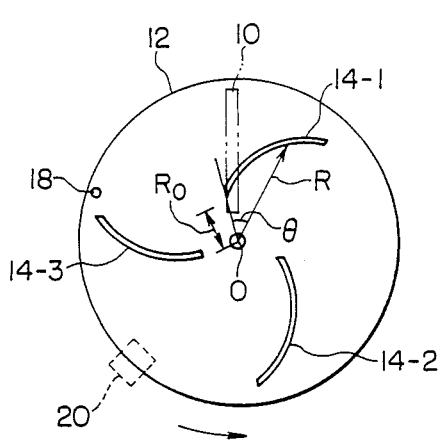
FIG. 2 is a plan view showing a first example of a slit disk in the optical scanning device of FIG. 1.

A slit disk 12 is placed over the outlet slit 10 of the spectroscope 8. As shown in FIG. 2, the slit disk 12 has, for instance, three slits 14-1, 14-2 and 14-3. The slits 14-1, 14-2 and 14-3 are so shaped that the distance R from the center 0 changes according to the following expression:

$$R = R_0 + k\theta$$

where $\theta$ is the angle of rotation, K is constant and $R_0$ is the distance between the center 0 and the innermost point of each slit.

The slit disk 12 is fixedly mounted on the rotary shaft of a motor 16 so that the disk is directly turned by the motor 16. The positional relationship between the slit disk 12 and the outlet slit 10 of the spectroscope 8 is as shown in FIG. 2. That is, the outlet slit 10 extends radially of the slit disk 12. The slit disk 12 has a hole 18 which is used for detecting the original point of the slits 14-1, 14-2 and 14-3. The detection is carried out by a detector 20 shown in FIG. 1.

The light beam which passes through the hole that is formed when one of the slits 14-1, 14-2 or 14-3 of the slit disk 12 is superimposed over the outlet slit 10 is applied through a spherical mirror 22 and a plane mirror 24 to a specimen plate 26. The specimen plate 26 is supported on a stage (not shown) that is movable in the X and Y directions. A half-mirror 23 is provided to reflect a part of the above-described light beam to an irradiation beam monitoring photomultiplier 27.

In order to detect the light beam that passes through the specimen plate 26, a detector 28-1, such as a photomultiplier, is employed. The detector 28-1 receives the light beam through a diffusion plate 29 such as a polytetrafluoroethylene plate.

A photomultiplier 28-2 detects light reflected from the specimen plate 26. A preamplifier 30 amplifies the output detection signal of the detector 28-1 and a logarithmic conversion amplifier converts the output signal of the preamplifier 30. An A/D (analog-to-digital) amplifier 34 converts the output signal of the logarithmic conversion amplifier 32 into a digital signal, and a CPU (central processing unit) 36 receives the digital signal to calculate the absorbancy and to control the pulse motor 16. The CPU utilizes the output signal of the detector 20 (such as a photo-coupler) and the angle of rotation of the slit disk 12 to determine a beam irradiation position on the specimen plate 26, and to perform locality correction.

Figure 3:
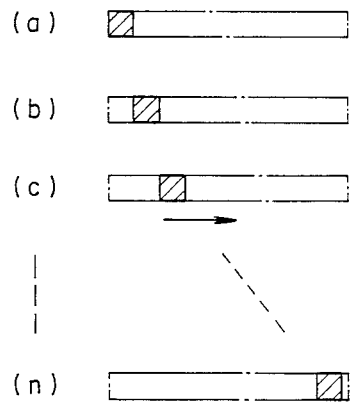
FIG. 3 is an explanatory diagram for a description of the movement of a light beam irradiation position on the specimen surface in the device of FIG. 1.

If, in FIG. 2, the slit disk 12 is turned in the direction of the arrow, the hole formed at the intersection of the outlet slit 10 and the slit 14-1 moves along the outlet slit 10 in such a manner that it moves away from the center of the slit disk 12. Thus, the beam irradiation position on the speciment plate 26 is moved as indicated by (a), (b), (c), . . . (n) in FIG. 3. When the slit disk 12 is further turned so that the next slit 14-2 intersects the outlet slit 10, the beam irradiation position on the specimen plate 26 returns to the position indicated by (a) in FIG. 3. Whenever the scanning of the specimen plate 26 with each of the slits 14-1, 14-2 and 14-3 is accomplished, the stage and accordingly the specimen plate 26 is moved by a predetermined distance in the Y direction. When an entire lane in the Y direction has been scanned as described above, the stage is moved in the X direction to start the next scanning operation.

Figure 4:
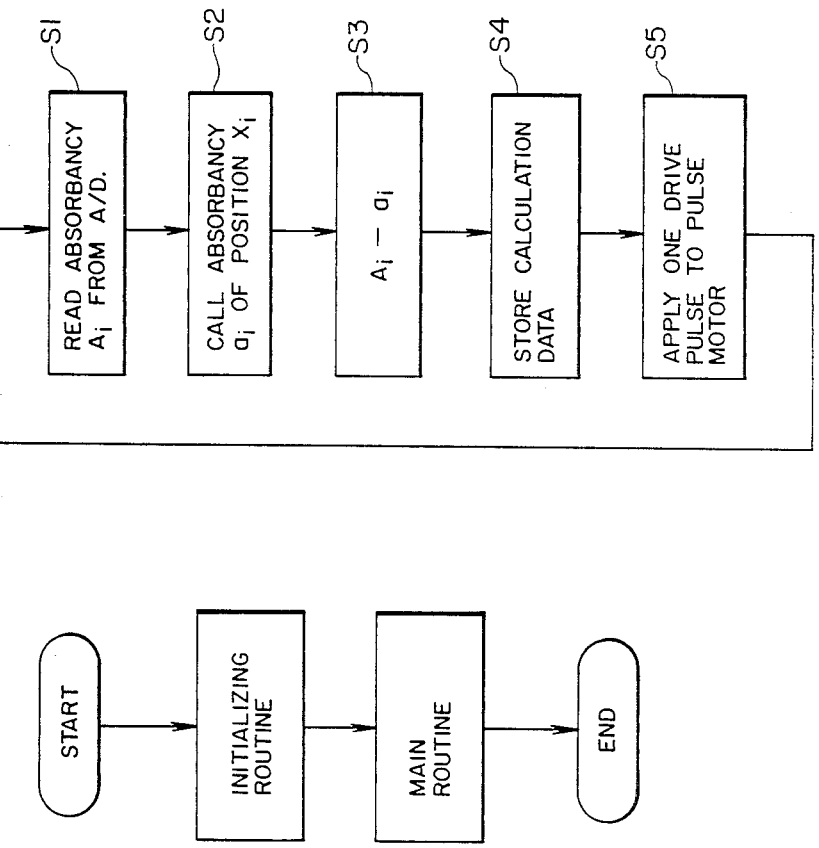

The procedure for locality correction as utilized by the present invention will be described with reference to FIGS. 4 and 5.

First, in the initializing routine, the stage is moved so that there is no specimen plate in the densitometer, and under this condition the slit disk 12 is turned to measure absorbancies $a_1$, $a_2$, $a_3$, . . . and $a_n$ respectively at positions $X_1$, $X_2$, $X_3$, . . . and $X_n$ and the measured data are stored. The CPU 36 utilizes the output signal of the original point detecting detector 20 and the angle of rotation of the pulse motor 16, i.e., the number of drive pulses of the pulse motor 16, in order to determine the positions $X_1$ through $X_n$.

Next, the stage is moved in the densitometer to set the specimen plate 26 at the measuring position, and measurement is performed for locality correction. The process is as shown in FIG. 5. When the measurement for a point Xi on the specimen plate 26 is performed, the CPU 36 reads the absorbancy Ai from the A/D converter 34 (Step S1), and calls the absorbancy ai of the position Xi which has been stored in the initializing routine, in order to calculate the difference between the two absorbancies Ai and ai (Steps S2 and S3). This is the locality correction.

After the calculated difference is stored (Step S4), one drive pulse (or a predetermined number of drive pulses) is applied to the pulse motor 16 to move the beam irradiation position on the specimen plate 26 (Step S5). And the locality correction is carried out for all the measurement points in the same manner.

In the above-described embodiment, only one hole 18 is formed in the slit disk, to detect the slit original point; however, as many holes as the number of slits (14-1 through 14-3) may be provided.

In the embodiment, three slits are formed in the slit disk 12; however, the invention is not limited thereto or thereby. For instance, two or more than three slits may be formed in the slit disk. Furthermore, only one slit may be formed in the slit disk. In this case, the pulse motor 16 may be reciprocated to move the slit backwards and forwards, so that the hole at the intersection of the slit and the outlet slit 10 is reciprocated along the outlet slit 10.

Moreover, in the embodiment, the slits of the slit disk 12 are arcuate; however, the invention is not limited thereto or thereby. That is, any configuration may be employed for the slits if the distance from the center changes with the angle of rotation $\theta$.

In FIG. 1, the slit disk 12 is placed over the outlet slit 10. The same effect can be obtained by the method in which the image formation in the X-direction is carried out on the outlet slit 10 while the image formation in the Y direction is carried out on the slit disk 12. Alternatively, the slit disk 12 may be set at the position where the image of the outlet slit 10 is formed. In addition, the slit disk 12 may be spaced from the outlet slit 10 to the extent that no trouble is caused in the measurement.

Instead of a pulse motor, a synchronous motor may be employed to rotate the slit disk. In this case, the angle of rotation of the slit disk 12 can be determined by detecting the period of time which elapses from the detection of the original point.

In the above-described chromatoscanner, no data are read during the period that the scanning line or lane, in the X or Y direction, on the specimen plate is changed, and therefore the slit disk may have angle ranges which are not covered by the slits. However, certain difficulties occur in the case where the photomultiplier receives a part of the light beam passing through the slit mechanism to detect the intensity of the light source, and the output of the photomultiplier is utilized to apply dynode feedback to another photomultiplier adapted to sample the light beam reflected from or passing through the specimen plate for automatic correction of the negative high voltage. For example, since no monitoring light beam is provided for the period of time corresponding to the angle range, a spike-shaped peak occurs instantaneously with the negative high voltage, i.e., the applied negative high voltage becomes maximum. Furthermore, since no light beam is applied to the photomultiplier adapted to sample the light beam reflected from or passed through the specimen plate, the output of the absorbancy calculating amplifier becomes abnormal.

The instantaneous rise of the negative high voltage may be eliminated by inserting a suitable response circuit in the negative high voltage circuit. This method, however, adversely affects the output signal of the sampling photomultiplier with the result that the stability of the light measuring system and the signal processing system is lowered.

These problems can be solved by also applying the light beam to the specimen for the period that the data of absorbancy of the specimen is not read. That is, the problem can be solved by the provision of a slit disk which, in the case where the light beam passing through the slit mechanism is monitored by the photomultiplier, eliminates the abrupt variation of the negative high voltage, i.e., the occurrence of a peak with the negative high voltage due to dynode feedback during the scanning period, so that the negative high voltage is maintained substantially uniform.

Figure 6:
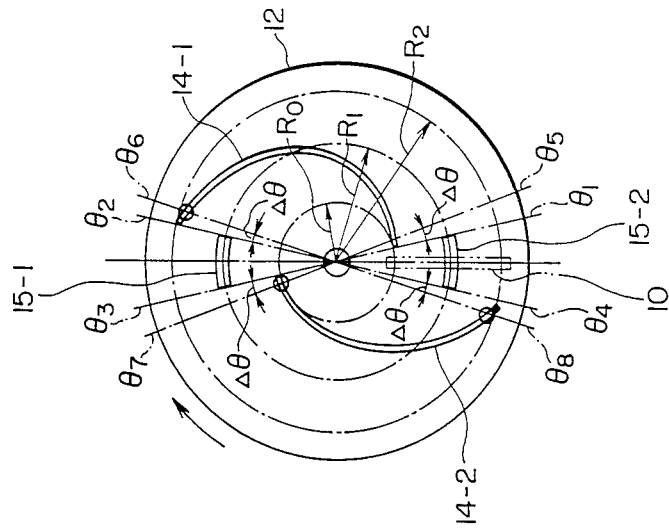
FIG. 6 is a plan view showing a second example of a slit disk for use in the optical scanning device of FIG. 1.

FIG. 6 is a plan view showing one example of the above-described slit disk in detail. As shown in FIG. 6, the rotary slit disk 12 has first slits 14-1 and 14-2 in which the distance from the center changes with the angle of rotation. Second slits 15-1 and 15-2 are provided which are separated from the first slits 14-1 and 14-2 but are continuous with the first slits in the angle of rotation. Similarly, as in the disk shown in FIG. 2, the slit disk 12 is mounted on the rotary shaft of the motor 16. The first slits 14-1 and 14-2 are used to read data as in the case of the slit disk of FIG. 2. That is, the first slits are formed as a spiral so that as the slit disk 12 turns the distance R from the center is increased from $R_0$ to $R_2$. The slit 14-1 covers an angle range $\theta_1$–$\theta_2$, and the slit 14-2 an angle range $\theta_3$–$\theta_4$.

The second slits 15-1 and 15-2 located between the first slits 14-1 and 14-2 are at the distance $R_1 = (R_0 + R_2)/2$ from the center, and are arcuate. The slit 15-1 covers an angle range $\theta_2$–$\theta_3$, and the slit 15-2 extends through an angle range $\theta_4$–$\theta_1$. Thus, the slits 14-1, 15-1, 14-2 and 15-2 cover the entire 360° angle range of the slit disk 12. Furthermore, the slit disk is so designed that the area of the hole formed by the rectangular slit 10 and each slit is maintained substantially unchanged during the revolution of the slit disk 12.

As the slit disk 12 is rotated in the direction of the arrow, the light beam is moved to scan the specimen plate 26. This will be described with reference to FIGS. 7 and 8.

Figure 7:
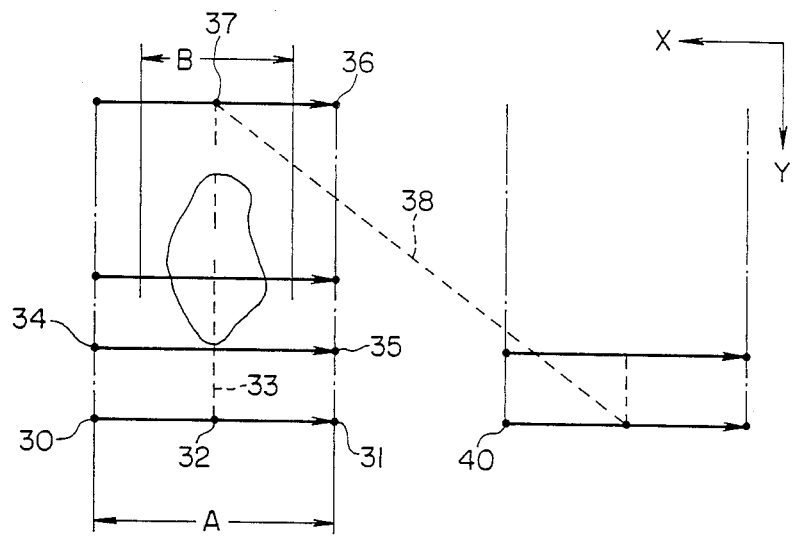
FIG. 7 is an explanatory diagram showing the movement of the light beam irradiation position on a specimen in a scanning operation.

It is assumed that when the line $\theta_1$ on the slit disk 12 reaches the rectangular slit 10, the beam irradiation point on the specimen plate 26 is at a position 30 in FIG. 7. As the slit disk 12 is rotated with the specimen plate 26 stopped, the hole formed at the intersection of the first slit 14-1 and the slit 10 is moved in such a manner that it slides away from the center, while the beam irradiation point on the specimen plate 26 is moved from the position 30 to a position 31 in FIG. 7. As the slit disk 12 is further rotated through a predetermined angle by the step motor 16, the beam irradiation point is moved by a predetermined distance. When the line $\theta_2$ on the slit disk reaches the rectangular slit 10, the slit 10 intersects the second slit 15-1. Therefore, the irradiation point on the specimen plate 26 is moved to a position 32. At the same time, the stage moves the specimen plate 26 by a predetermined distance in the Y direction. As a result, the irradiation point is moved on the specimen plate 26 as indicated by the broken line in FIG. 7.

When the line $\theta_3$ reaches the rectangular slit 10, the slit 10 intersects the slit 14-2, so that the irradiation point on the specimen plate 26 is at a position 34. As the slit disk 12 is rotated in the direction of the arrow with the specimen plate 26 held stopped, the irradiation point is moved to point 35. The slit disk 12 is rotated repeatedly in the above-described manner. When the irradiation point reaches a position 36 in FIG. 7, the scanning operation of one lane is completed.

Under the condition that the rectangular slit 10 intersects the slit 15-1 or 15-2, the slit disk 12 is held stopped and the lane is changed. In this case, the irradiation point on the specimen plate 26 is at a position 37 in FIG. 7. The specimen plate 26 is moved a predetermined distance in the X-direction and a predetermined distance in the Y direction, so that the irradiation point is moved as indicated by the broken line 38 in FIG. 7. Under this condition, the slit disk 12 is turned again. When the first slit 14-1 or 14-2 intersects the rectangular slit 10, the irradiation point is moved to a scan start position 40. Thus, a new lane can be scanned in the same manner.

While the data are being read, the hole at the intersection of the first slit 14-1 or 14-2 and the rectangular slit 10 moves radially of the slit disk in such a manner that the distance from the center changes from $R_0$ to $R_2$. However, it is preferable that the actual data reading period be limited to an angle range which is defined by two points on the slits 14-1 or 14-2 which are slightly away from both ends of the slit, i.e., an angle range $\theta_5$–$\theta_6$ in the case of the slit 14-1, and an angle range $\theta_7$–$\theta_8$ in the case of the slit 14-2. This is because in angle ranges $\Delta\theta$ at both ends of each slit trouble is liable to occur; for instance, the data may be erroneously read and the measuring circuit may become excessively sensitive.

Even for the scanning line changing period indicated by the broken line 33 and the line changing the period indicated by the broken line 38, the specimen plate 26 is kept irradiated, and therefore the photomultipliers 28-1 and 28-2 provide the output signals; however, the output signals are not read as data.

As is apparent from the above description, the light beam emerging from the hole at the intersection of the rectangular slit 10 and each of the slits 14-1, 14-2, 15-1, and 15-2 is continuously applied to the specimen plate with a substantially constant intensity. Accordingly, the light beam applied to the monitoring photomultiplier 27 is also substantially constant in intensity. Therefore, even when the output of the photomultiplier 27 is utilized to apply dynode feedback to the other photomultipliers 28-1 and 28-2 for automatic correction of the negative high voltage, no abrupt peak occurs with the negative high voltage, and, therefore, the measurement can be performed with a negative high voltage that is substantially uniform in level. Furthermore, since the light beam applied to the specimen plate 26 is also substantially constant in intensity as described above, the output of the absorbancy calculating amplifier receiving the output signals of the photomultipliers 28-1 and 28-2 are normal at all times.

It is recommended that, after the scanning operation has been accomplished, the slit disk 12 be stopped with the slit 15-1 or 15-2 intersected with the rectangular slit 10, to readily detect the center of the beam scanning range.

In the above-described embodiment, the radius of curvature $R_1$ of the second slits 15-1 and 15-2 is expressed by $(\frac{1}{2}(R_2 + R_0)$ where $R_0$ and $R_2$ are the start point curvature radius and the finish point curvature radius of the first slits 14-1 and 14-2, respectively. Therefore, the mechanical strength of the central part of the slit disk 12 is maintained high, and the slit disk 12 itself is high in rigidity.

Figure 8:
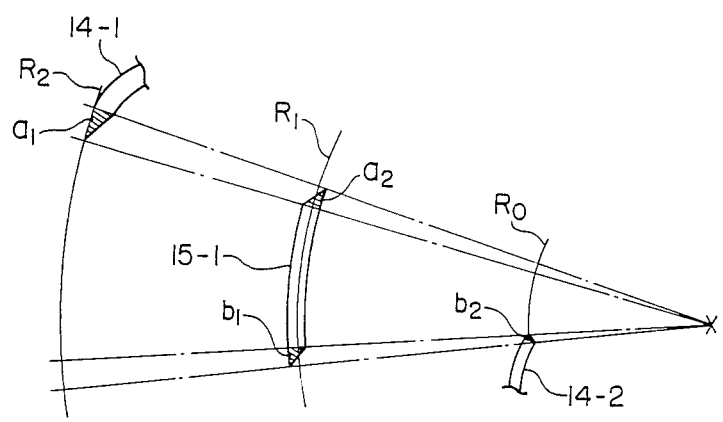
FIG. 8 is a diagram showing a third example of an optical disk for use in the device of the present invention in which the first and second slits optically overlap one another at the ends.

FIG. 8 shows another example of the optical coupling part of the first and second slits formed in the slit disk 12. In the slit disk 12 shown in FIG. 6, the first slits 14-1 and 14-2 are optically coupled with the second slits 15-1 and 15-2 with the slit ends arranged on the respective lines $\theta_1$, $\theta_2$, $\theta_3$ and $\theta_4$. In the slit disk of FIG. 8, the slits 14-1 and 14-2 are optically coupled to the slits 15-1 and 15-2 in such a manner that the ends of the former overlap the ends of the latter. In this case, the overlapping parts $a_1$, $a_2$, $b_1$, $b_2$... should be equal in area to one another.

The slit disk of FIG. 8 is free from the difficulty that the coupling parts of the first and second slits intercept the irradiating light beam in the event of errors in manufacturing.

The number and configuration of slits formed in the slit disk are not limited to those shown in FIGS. 7 and 8.

The measuring systems (27 through 36) in FIG. 1 will be described in detail with reference to FIG. 9.

Figure 9:
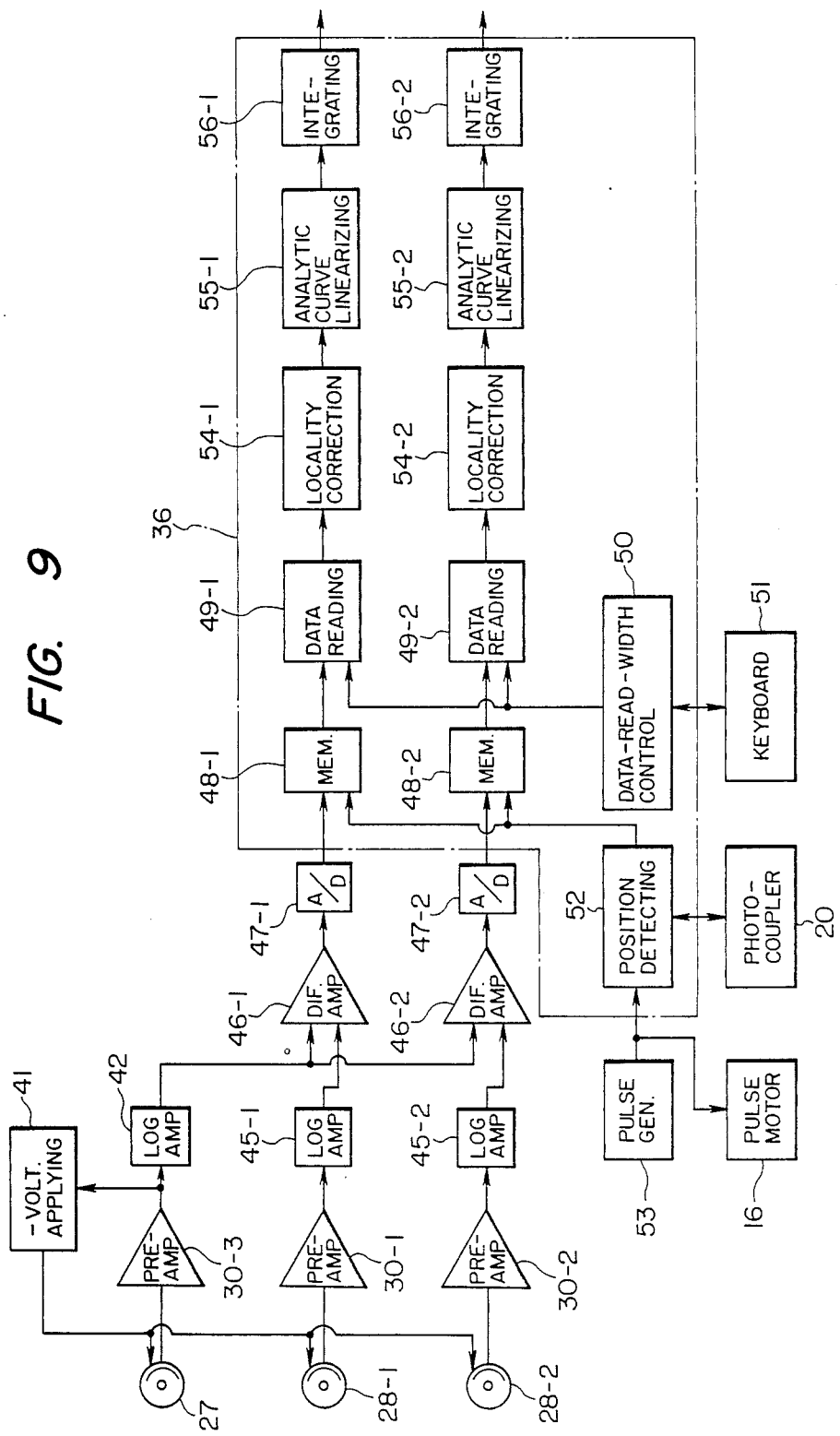
FIG. 9 is a block diagram showing a measuring system in the optical scanning device of FIG. 1.

In FIG. 9, reference numeral 30-3 designates a preamplifier for amplifying the detection signal of the light source monitoring photomultiplier 27. A negative high voltage applying means 41 applies a predetermined negative high voltage to the photomultipliers 27, 28-1 and 28-2 according to the output of the preamplifier 30-3. The means 41 includes, for instance, a DC-DC converter. The output signal of the preamplifier 30-3 is converted into a logarithmic value by a logarithmic conversion amplifier 42.

The output of the reflected beam measuring photomultiplier 28-1 is applied through a preamplifier 30-1 to a logarithmic conversion amplifier 45-1. The difference between the outputs of the amplifiers 45-1 and 42 is outputted by an amplifier 46-1, and converted into a digital signal by an A/D converter 47-1.

Similarly, the output signal of the transmitted beam measuring photomultiplier 28-2 is applied through a preamplifier 30-2 to a logarithmic conversion amplifier 45-2, where it is converted into a logarithmic value. The difference between the output signals of the logarithmic conversion amplifiers 45-2 and 42 is outputted by an amplifier 46-2, and converted into a digital signal by an A/D converter 47-2. In this manner, the absorbancies are converted into digital signals by the A/D converters 47-1 and 47-2. The digital data together with the data of the position on the specimen plate supplied by a position detecting means 52 are stored in memory means (RAMs) 48-1 and 48-2, respectively.

The position data is provided by the position detecting means 52 as follows. The output signal of the detector 20, such as a photo-coupler adapted to detect the original point of the angle of rotation of the slit disk 12, is employed as a reference. The output pulse of a pulse generating circuit 53 adapted to drive the pulse motor 16 is connected, so that the position data is outputted by the position detecting means 52.

Further in FIG. 9, data reading means 49-1 and 49-2 are provided for reading absorbancy data stored in the memory means 48-1 and 48-2, respectively. The ranges of data read by the data leading means 49-1 and 49-2 are specified by a signal provided by a data-read-width control means 50. More specifically the data-read-width control means 50 applies the signal to the data reading means 49-1 and 49-2 according to the value set with a keyboard 51 which is a data-read-width setting means.

The data read by the data reading means 49-1 and 49-2 are subjected to locality correction by locality correcting means 54-1 and 54-2. The outputs of the locality correcting means 54-1 and 54-2 are applied to analytic curve linearizing means 55-1 and 55-2, where they are converted into densities. The outputs of the analytic curve linearizing means 55-1 and 55-2 are outputted, after being integrated by integrating means 56-1 and 56-2. The term "locality" is intended to mean the variation in sensitivity of the detector which depends on location, or the variation in brightness of the optical system which depends on location. The term "analytic curve linearization" is intended to mean the correction of the relationship between absorbancy and density into a linear one.

The part surrounded by the chain line in FIG. 9 corresponds to the CPU 36 in FIG. 1.

The operation of the measuring system shown in FIG. 9 will be described. In the light beam scanning operation carried out with the rotary slit disk 12 shown in FIG. 2, the scanning width A (FIG. 7) is constant and is determined from the configuration of the slits 14-1 through 14-3. The absorbancy data at various data detecting positions in the scanning width A are stored in the memory means 48-1 and 48-2 together with the respective position data. Of the absorbancy data thus stored, only the portion defined by the range B (FIG. 7), which is set by the keyboard 51, is read as effective data by the data reading means 49-1 and 49-2. That is, the measuring system of FIG. 9 processes only the effective data.

The slit disk of FIG. 6 is mechanically devised so that, when the light source intensity is monitored to apply dynode feedback to the photomultipliers for automatic correction of the negative high voltage, the monitoring light beam may not be intercepted. On the other hand, in the measuring system of FIG. 9, the data provided when the monitoring light beam is intercepted are electrically made ineffective, so that only effective data are used for photometric operation, monitoring the light source intensity, and dynode feedback control.

Although the locality correction has been described with reference to FIGS. 4 and 5, it will be described again with reference to FIG. 9 and FIGS. 4 and 5.

In the initializing routine, the stage is moved so that specimen plate is in the densitometer, and under this condition the slit disk 12 is turned to measure absorbancies $a_1$, $a_2$, $a_3$, ... and $a_n$, respectively, at positions $X_1$, $X_2$, $X_3$, ... and $X_n$ thereof and store the data thus measured. These positions $X_1$ through $X_n$ are detected by the position detecting means 52 by utilizing the detection signal of the photo-coupler 20, and the angle of rotation of the pulse motor 16, i.e., the number of drive pulses of the pulse motor 16.

Next, the stage is moved to set the specimen 26 at the measuring position, and measurement is performed for locality correction.

Figure 5:
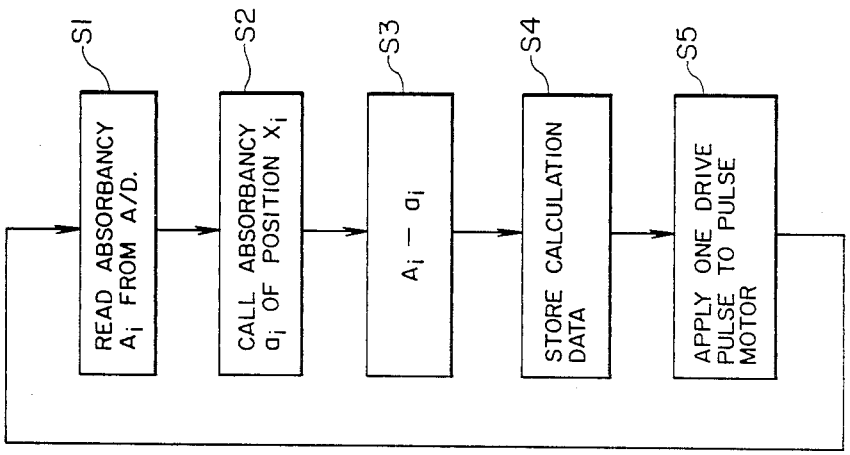
FIGS. 4 and 5 are flow charts for a description of locality correction in the device of FIG. 1.

The process for locality correction is as shown in FIG. 5. When the data reading means 49-1 and 49-2 read from the memory means 48-1 and 48-2 an absorbancy Ai at a point Xi on the specimen plate 26 (Step S1), the absorbancy ai of the position Xi which has been measured and stored in the initializing routine is accessed, so that the difference between the two absorbancies is calculated (Steps S2 and S3). The locality correction is carried out as described above. The difference thus calculated is stored in another memory means (Step S4). Thereafter, one drive pulse or a predetermined number of drive pulses are applied to the pulse motor 16 to move the beam irradiation position on the specimen plate 26 (Step 5). Locality correction is carried out for all of the measurement points in the same manner.

Analytic curve linearization is carried out with an analytic curve linearizer program system using a microcomputer according to Rubelka-Munk's theoretical formula indicating absorbancy with material density. The analytic curve linearization is well known in the art, being described in detail, for instance, in the "Journal of Chromatography", vol. 116, pp. 22 to 41.

As was described before, in the scanning width A on the specimen plate 26, the range B is selected as the area wherein the data are effective. The data outside the range B may be used as specimen plate's background absorbing data, to obtain the absorbancy difference from the other effective data.

In the above-described embodiment, both the absorbancy of the light beam reflected from the specimen plate and the absorbancy of the light beam passing through the specimen plate are measured. However, substantially the same effect can be obtained by measuring only one of the two absorbancies.

As is apparent from the above description, according to the present invention, the specimen plate can be scanned with the light beam by rotating the compact slit disk in one direction or alternately clockwise and counterclockwise. Therefore, the chromatoscanner of the invention is simple in construction, and high in scanning speed. As the slit disk is driven directly by the pulse motor or synchronous motor, the slit disk is high in durability. Furthermore, as the beam irradiation position on the specimen plate can be detected from the angle of rotation of the motor, locality correction can be readily achieved.

When the chromatoscanner of the present invention operates at high scanning speed, the irradiating light beam is not interrupted although the slits formed in the slit disk are discontinuous from one another. Therefore, in the monitoring system or detecting system comprising a photomultiplier of dynode feedback type, an abrupt increase of the negative high voltage is prevented. That is, the intensity of the light beam applied to the monitoring photomultiplier is maintained substantially constant with the results that the negative high voltage is held substantially constant and the detecting sensitivity is also substantially constant.

The use of the slit disk of the present invention allows the photomultiplier to continuously provide the output signal. Therefore, it is unnecessary to modify the photometric signal detecting system, and correct absorbancy values are detected at all times. Moreover, when the scanning of the specimen plate is suspended, the scanning beam can be set at the center of the scanning width. Therefore, the scanning beam can be readily positioned with respect to the specimen plate.

It should be understood that the present invention is not limited to the particular embodiment described, but rather is susceptible to modifications, alterations, and equivalent arrangements within the scope of the appended claims.

What is claimed is:

1. A chromatoscanner for scanning a specimen surface comprising:
   a spectroscope having an elongated outlet slit for producing a light beam in the elongate shape of said outlet slit;
   a rotatable disk having a slit therethrough beginning a selected distance from the center of said disk and extending to a point adjacent the periphery of the disk, said disk being mounted between said elongated outlet slit and the specimen and disposed to intersect said elongated beam of light, said slit being configured to pass a different portion of said elongated beam to scan the specimen upon rotation of said disk to rotate said slit through said elongated beam of light;
   means for rotating said disk, the position of said portion of said elongated beam passing through said slit changing relative to the center of said disk, upon angular rotation of said disk, to perform an individual scan of said specimen along a discrete scan path each time said slit rotates past said elongated outlet slit;
   means for generating absorbancy data for each of said individual scans of the specimen by measuring the degree of transmission of said light beam through the specimen along each of said discrete scan paths;
   position detecting means for producing position data corresponding to the position of each of said discrete scan paths by measuring the angle of rotation of said disk by said rotating means;
   memory means for storing said absorbancy data and said position data corresponding to each of said discrete scan paths;
   data reading control means for selecting a part of each individual scan path for which absorbancy data is read; and
   data reading means for reading said selected absorbancy data from said memory means in accordance with said position data stored in said memory means.

2. A chromatoscanner according to claim 1, wherein said slit in said rotatable disk is arcuate.

3. A chromatoscanner according to claim 1, further including means for selectively setting the length of each discrete scan path.

4. A chromatoscanner according to claim 1, further including illumination control means for determining the illumination level of the specimen by said elongated beam of light and for controlling said absorbancy data generating means to compensate for variations in said illumination level.

5. A chromatoscanner according to claim 4, wherein said rotating means comprises a pulse motor and said position detecting means is adapted to produce said position data in accordance with the number of pulses supplied to said pulse motor.

6. A chromatoscanner according to claim 4, wherein said rotating means comprises a synchronous motor and said position detecting means is adapted to produce said position data in accordance with the duration of operation of said synchronous motor.

7. A chromatoscanner for scanning a specimen surface comprising:
   a spectroscope having an elongated outlet slit for producing a light beam in the elongate shape of said outlet slit;
   a rotatable disk having two or more spaced-apart slits therethrough beginning a selected distance from the center of said disk and extending to a point adjacent the periphery of said disk, said disk being mounted between said elongated outlet slit and the specimen and disposed to interesect said elongated beam of light, said spaced-apart slits being configured to pass a different portion of said elongated beam to scan the specimen upon rotation of said disk to rotate said spaced-apart slits through said elongated beam of light;

means for rotating said disk, the position of said portion of said elongated beam passing through each of said spaced-apart slits changing relative to the center of said disk, upon angular rotation of said disk, to perform an individual scan of said specimen along a discrete scan path each time each of said spaced-apart slits rotates past said elongated outlet slit;

means for generating absorbancy data for each of said individual scans of the specimen by measuring the degree of transmission of said light beam through the specimen along each of said discrete scan paths;

position detecting means for producing position data corresponding to the position of each of said discrete scan paths by measuring the angle of rotation of said disk by said rotating means;

memory means for storing said absorbancy data and said position data corresponding to each of said discrete scan paths;

data reading control means for selecting a part of each individual scan path for which absorbancy data is read; and data reading means for reading said selected absorbancy data from said memory means in accordance with said position data stored in said memory means.

8. A device according to claim 7, wherein said rotatable disk further includes a plurality of illumination slits singly disposed between said spaced-apart slits and being radially separate from said spaced-apart slits.

9. A device according to claim 8, wherein each of said illumination slits is angularly coterminous with said spaced-apart slits.

* * * * *